United States Patent [19]
Englert et al.

[11] Patent Number: 5,292,755
[45] Date of Patent: Mar. 8, 1994

[54] USPA BENZOLYGUANIDINES

[75] Inventors: Heinrich C. Englert; Hans-Jochen Lang, both of Hofheim am Taunus; Wolfgang Linz, Mainz; Bernward Schölkens, Kelkheim; Wolfgang Scholz, Eschborn, all of Fed. Rep. of Germany

[73] Assignee: Hoechst Aktiengesellschaft, Frankfurt am Main, Fed. Rep. of Germany

[21] Appl. No.: 830,355

[22] Filed: Jan. 31, 1992

Related U.S. Application Data

[62] Division of Ser. No. 576,937, Sep. 4, 1990, Pat. No. 5,091,394.

[30] Foreign Application Priority Data

Sep. 6, 1989 [DE] Fed. Rep. of Germany ....... 3929582

[51] Int. Cl.$^5$ ............... A61K 31/445; C07D 211/28; C07C 279/10
[52] U.S. Cl. ........................... 514/331; 546/231; 546/149; 546/164; 546/172; 546/193; 548/300.1; 548/491; 548/563; 548/313.7; 564/85; 564/237; 514/183; 514/212; 514/237.8; 514/255; 514/275; 514/307; 514/311; 514/316; 514/400; 514/415; 514/427; 514/603; 514/604; 540/483; 540/610; 544/158; 544/159; 544/332; 544/393
[58] Field of Search ............... 544/158, 159, 393, 332; 540/483, 610; 546/149, 164, 172, 193, 231; 548/339, 491, 563; 564/85, 237; 514/307, 311, 316, 331, 237.8, 255, 275, 400, 415, 427, 603, 634, 212, 183

[56] References Cited

U.S. PATENT DOCUMENTS

| | | | |
|---|---|---|---|
| 3,432,551 | 3/1969 | Garzia | 564/237 |
| 3,780,027 | 12/1973 | Cragoe | 549/494 |
| 3,953,476 | 4/1976 | Cragoe | 549/494 |
| 4,178,387 | 12/1979 | Diamond et al. | 564/237 |

FOREIGN PATENT DOCUMENTS

2643952A1 4/1977 Fed. Rep. of Germany.
882090 2/1959 United Kingdom.

OTHER PUBLICATIONS

Tammiso et al "Sedative 3,4,5-Trimethoxybenzoyl-N,-N'-Diethyl guanidine in Animals" CA 81: 58245x (1974).
Schmid et al "Sodium/H Ion Exchange in Poreine Cerebral Capillary Endothelial Cells" CA 47(1)4775p (1992).
Resmick, B. M. "Fungicidal use of 1-(Alkoxyaroyl-)-Guanidines" CA 94(25)203827 (1981).
Matsumoto et al "Effect of Guanidino Compounds on Choline Acetyltrausyerase and Actzlcholinesterase of Rabbit Brain" CA 89: 70774s (1978).
Duff, et al., "Amiloride. Antiarrhythmic and Electrophysiologic Actions in Patients with Inducible Sustained Ventricular Tachycardia," Circulation, vol. 79, No. 6, pp. 1257-1263, published Jun. 1989.
Buschauer, "Synthesis and in Vitro Pharmacology of Arpromidine and Related Phenyl(pyridylalkyl)guanidines, a Potential New Class of Positive Inotropic Drugs," Journal of Medicinal Chemistry, No. 8, pp. 1963-1970, Aug. 1989.

Primary Examiner—C. Warren Ivy
Assistant Examiner—Celia Chang
Attorney, Agent, or Firm—Finnegan, Henderson, Farabow, Garrett & Dunner

[57] ABSTRACT

Benzoylguanidines of the formula I

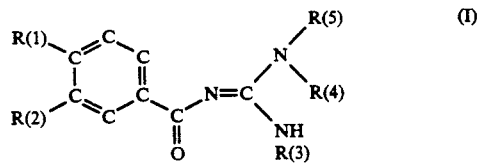

where
R(1) or R(2) is equal to R(6)—S(O)$_n$— or R(7)R(8)N—O$_2$S—
and the other substituent R(1) or R(2) is in each case (Abstract continued on next page.)

equal to H, F, Cl, Br, I, alkyl, alkoxy or phenoxy, $R(6)-S(O)_n$ or $R(7)R(8)N-$ and R(6) is equal to alkyl, cycloalkyl, cyclopentylmethyl, cyclohexylmethyl or phenyl, R(7) and R(8) are equal to alkyl or phenylalkyl or phenyl, and in which R(7) and R(8) may also together be a $C_4-C_7$ chain, and in which R(7) and R(8), together with the nitrogen atom to which they are bonded, may be a dihydroindole, tetrahydroquinoline or tetrahydroisoquinoline system, and where R(3), R(4) and R(5) are equal to hydrogen or alkyl, or R(3) and R(4) are together an alkylene chain or R(4) and R(4) are together an alkylene chain, and where n is equal to zero, 1 or 2 and their pharmaceutically tolerable salts are outstanding antiarrhythmics.

4 Claims, No Drawings

USPA BENZOYLGUANIDINES

This is a division of application Ser. No. 07/576,937, filed Sep. 4, 1990, now U.S. Pat. No. 5,091,394 issued Feb. 25, 1992.

The invention relates to benzoylguanidines of the formula I

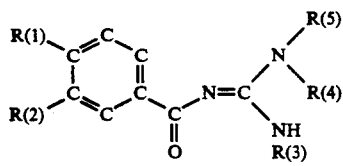

in which R(1) or R(2) is R(6)—S(O)$_n$— or and the other substituent in each case, R(1) or R(2), is H, F, Cl, Br, I, $C_1$-$C_4$-alkyl, $C_1$-$C_4$-alkoxy, phenoxy which is unsubstituted or carries one to three substituents from the groups fluorine, chlorine, methyl or methoxy, R(6)—S(O)$_n$ or

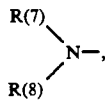

and in which $R^6$ is $C_1$-$C_6$-alkyl, $C_5$-$C_7$-cycloalkyl, cyclopentylmethyl, cyclohexylmethyl or phenyl which is unsubstituted or carries one to three substituents from the groups fluorine, chlorine, methyl or methoxy, and in which R(7) and R(8) are identical or different and have the meaning H or $C_1$-$C_6$-alkyl or R(7) is phenyl-(CH$_2$)$_m$— where m=1-4, or phenyl which is unsubstituted or carries one or two substituents from the groups fluorine, chlorine, methyl or methoxy, and in which R(7) and R(8) can also together be a straight-chain or branched $C_4$-$C_7$ chain, it being possible for the chain to be additionally interrupted by O, S or NR(9) and R(9) being H or methyl, and in which R(7) and R(8), together with the nitrogen atom to which they are bonded, can be a dihydroindole, tetrahydroquinoline or tetrahydroisoquinoline system, and R(3), R(4) and R(5) are hydrogen or $C_1$-$C_2$-alkyl, or where either R(3) and R(4) can together form a ($C_2$-$C_4$)-alkylene chain or R(4) and R(5) can together form a ($C_4$-$C_7$)-alkylene chain, and n is zero, 1 or 2, and their pharmaceutically tolerable salts.

If the substituents R(1) to R(5) contain one or more centers of asymmetry, the invention includes compounds having both the S and R configuration. The compounds can be present as optical isomers, as diastereoisomers, as racemates or as mixtures thereof.

The alkyl radicals indicated can be both straight-chain and branched.

Preferred compounds of the formula I are those in which R(1) is fluorine, chlorine, NR(7)R(8), R(6)—S-(O)$_n$— or phenoxy, R(2) is R(6)—S(O)$_n$— and R(7)R(8)N—SO$_2$— and in which n is zero, 1 or 2 and R(3), R(4) and R(5) are hydrogen, and in which R(6), R(7) and R(8) have the abovementioned meaning, and their pharmacologically tolerable salts.

Particularly preferred compounds of the formula I are those where R(1) has the meaning R(7)R(8)N— or R(6)—S(O)$_n$—, in which R(6) is alkyl having 1-3 carbon atoms or phenyl, n=zero and R(7) and R(8) are hydrogen or alkyl having 1-4 carbon atoms, or R(7) and R(8) together form a ($C_4$-$C_7$)-methylene chain and R(2) is $CH_3$—$CO_2$— or $H_2N$—$SO_2$—, R(3), R(4) and R(5) are equal to hydrogen, and their pharmacologically tolerable salts.

Very particularly preferred compounds are 3-methylsulfonyl-4-(1-piperidinyl)benzoylguanidine, 4-phenylthio-3-sulfamoylbenzoylguanidine and 3-methylsulfonyl-4-phenylthiobenzoylguanidine and their pharmacologically tolerable salts.

The compounds I are substituted acylguanidines.

A prominent ester representative of the acylguanidines is the pyrazine derivative amiloride, which is used as a potassium-sparing diuretic in therapy. Numerous other compounds of the amiloride type are described in the literature, such as, for example, dimethylamiloride or ethylisopropylamiloride.

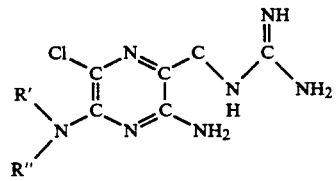

Amiloride: R' and R''=H
Dimethylamiloride: R' and R''=$CH_3$
Ethylisopropylamiloride: R'=$C_2H_5$ and R''=$CH(CH_3)_2$ Moreover, investigations have been disclosed which indicate antiarrhythmic properties of amiloride (Circulation 79, 1257-63 (1989)). However, a wide use as an antiarrhythmic is opposed by the fact that this effect is only weakly pronounced and occurs accompanied by a hypotensive and saluretic action, and these side effects are undesired in the treatment of cardiac arrhythmias.

Indications of antiarrhythmic properties of amiloride were also obtained in experiments on isolated animal hearts (Eur. Heart J. 9 (suppl. 1): 167 (1988) (book of abstracts)). Thus, for example, it was found in rat hearts that it was possible to suppress completely an artificially induced ventricular fibrillation by means of amiloride. Even more potent than amiloride in this model was the abovementioned amiloride derivative ethylisopropylamiloride.

In U.S. Pat. No. 3,780,027, acylguanidines are claimed which are structurally similar to the compounds of the formula I. The crucial difference to the compounds I is that they are trisubstituted benzoylguanidines which, in their substitution pattern, are derived from commercially available diuretics, such as bumetanide and furosemide, and carry an amino group important for the saluretic action desired in position 2 or 3 to the carbonylguanidine group. Correspondingly, a strong saluretic activity is reported for these compounds.

It was therefore very surprising that the compounds according to the invention have no undesired saluretic properties, but very good antiarrhythmic properties. Owing to their pharmacological properties, the compounds are outstandingly suitable as antiarrhythmic pharmaceuticals having a cardioprotective component, for infarct prophylaxis and infarct treatment and also for the treatment of angina pectoris, it also being possible to employ them preventively.

The invention furthermore relates to a process for the preparation of the compounds I, which comprises reacting compounds of the formula II

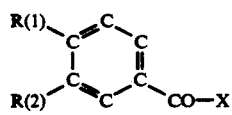

with a guanidine derivative of the formula III

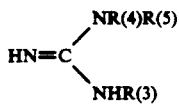

in which R(1) to R(5) have the meaning given and X is a leaving group which can easily be substituted by a nucleophile.

The activated acid derivatives of the formula II, in which X is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the carboxylic acid chlorides (formula II, X=Cl) on which they are based which, for their part, can in turn be prepared from the carboxylic acids (formula II, X=OH) on which they are based, for example with thionyl chloride.

In addition to the carboxylic acid chlorides of the formula II (X=Cl), other activated acid derivatives of the formula II can also be prepared in a known manner directly from the benzoic acid derivatives (formula II, X=OH) on which they are based, such as, for example, the methyl esters of the formula II where X=OCH$_3$ by treating with gaseous HCl in methanol, the imidazolides of the formula II by treating with carbonyldiimidazole (X=1-imidazolyl, Staab, Angew. Chem. Int. Ed. Engl. 1, 351-367 (1962)), the mixed anhydrides II with Cl—COOC$_2$H$_5$ or tosyl chloride in the presence of triethylamine in an inert solvent, and also the activation of benzoic acids with dicyclohexylcarbodiimide (DCC). A number of suitable methods for the preparation of activated carboxylic acid derivatives of the formula II are given with an indication of source literature in J. March, Advanced Organic Chemistry, 3rd edition (John Wiley & Sons, 1985), p. 350. A further method for the preparation, in particular of those compounds of the formula I in which R(4) and/or R(5) are not H, consists in the reaction of an acid chloride or other suitable activated benzoic acid derivative of the formula II with 3,5-dimethylpyrazole-1-carboxamidine nitrate (obtainable from Aldrich) in the presence of sodium hydroxide solution and subsequent treatment of the N-benzoyl-3,5-dimethylpyrazole-1-carboxamidine derivative with ammonia or an amine HNR(4)R(5) (Methods Enzymol. 25b, 558 (1972)).

The reaction of an activated carboxylic acid derivative of the formula I with a guanidine derivative of the formula III is carried out in a manner known per se in a protic or aprotic polar, but inert, organic solvent. In this connection, methanol or THF between 20° C. and the boiling point of these solvents have proven suitable for the reaction of the methylbenzoate (II, X=OMe) with guanidine. In most reactions of compounds II with salt-free guanidines III, the reaction was advantageously carried out in aprotic inert solvents such as THF, dimethoxyethane or dioxane. However, water can also be used as a solvent in the reaction of II and III.

If X is Cl, the reaction is advantageously carried out with the addition of an acid entrainer, for example in the form of excess guanidine, to remove the hydrohalic acid.

Some of the basic benzoic acid derivatives of the formula II and the guanidines of the formula III used are known and described in the literature. The unknown compounds of the formula II can be prepared by methods which are known from the literature by converting, for example, 4-chloro- or 4-fluoro-3-chlorosulfonylbenzoic acid with ammonia or an amine into a 3-aminosulfonyl-4-chloro-or -fluorobenzoic acid (IVa) or with a weak reductant such as sodium bisulfite and subsequent alkylation into a 3-alkylsulfonyl-4-chloro- or -4-fluorobenzoic acid (IVb, n=2)

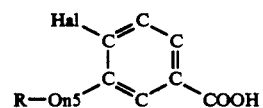

IVa): R = R(6)
IVb): R = NR(7)R(8)

and reacting the benzoic acids obtained by one of the process variants described above to give compounds I according to the invention.

However, compounds of the formulae (IVa) and b) can also be used as starting compounds for other carboxylic acids, it being very convenient to replace the halogen in the R(1) position by numerous nucleophilic reagents, such as mercaptans R(6)—SH or primary amines R(7)R(8)NH with the formation of other benzoic acid derivatives II where X=OH. In a similar manner, other benzoic acid derivatives (II, X=OH) can be prepared starting from 3-nitro-4-chlorobenzoic acid by nucleophilic introduction of a radical R(1) according to the invention in position 4 (replacement by Cl) and further modification of the nitro group, such as reduction to NH$_2$ and subsequent alkylation or displacement, for example by diazotization and Sandmeyer reaction.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methylsulfonates and p-toluenesulfonates.

Pharmaceuticals which contain a compound I can be administered orally, parenterally, intravenously, rectally or by inhalation, the preferred administration being dependent on the particular clinical picture of the disorder. In this connection, the compounds I can be used alone or together with pharmaceutical auxiliaries, and indeed both in veterinary and in human medicine.

Which auxiliaries are suitable for the desired pharmaceutical formulation is familiar to the person skilled in the art on the basis of his expert knowledge. In addition to solvents, gel-forming agents, suppository bases, tablet auxiliaries and other active compound carriers, antioxidants, dispersants, emulsifiers, defoaming agents, flavor correctors, preservatives, solubilizers or colorants, for example, can be used.

For a form for oral use, the active compounds are mixed with the additives suitable for this purpose, such as excipients, stabilizers or inert diluents and are brought into the forms suitable for administration, such as tablets, coated tablets, hard gelatin capsules, aqueous, alcoholic or oily solutions, by the customary methods. Inert carriers which can be used are, for example, gum arabic, magnesia, magnesium carbonate, potassium phosphate, lactose, glucose or starch, in particular cornstarch. In this case, preparation can take place both as dry and as moist granules. Suitable oily excipients or solvents are, for example, vegetable or animal oils, such as sunflower oil or cod liver oil.

For subcutaneous or intravenous administration, the active compounds, if desired with the substances customary for this purpose such as solubilizers, emulsifiers or other auxiliaries, are brought into solution, suspension or emulsion. Possible solvents are, for example: water, physiological saline solution or alcohols, for example ethanol, propanol, glycerol, in addition also sugar solutions such as glucose or mannitol solutions, or, alternatively, a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation may also contain other pharmaceutical auxiliaries such as surfactants, emulsifiers and stabilizers and also a propellant gas. Such a preparation customarily contains active compound in a concentration of about 0.1 to 10, in particular of about 0.3 to 3, % by weight.

The dosage of the active compound of the formula I to be administered and the frequency of administration depend on the potency and duration of action of the compounds used; and additionally also on the nature and severity of the disease to be treated and on the sex, age, weight and individual responsiveness of the mammal to be treated.

On average, the daily dose of a compound of the formula I in a patient of about 75 kg weight is at least 0.001 mg, preferably 0.01 mg to at most 10 mg, preferably at most 1 mg. In acute outbreaks of the illness, for example immediately after suffering a cardiac infarct, still higher and, above all, more frequent dosages may also be necessary, for example up to 4 individual doses per day. In particular on i.v. use, for example in an infarct patient in the intensive care unit, up to 100 mg per day may be necessary.

The compounds of the formula I according to the invention or their physiologically tolerable salts shown below can be prepared analogously to the procedures given in the exemplary embodiments:
4-methoxy-3-methylsulfonylbenzoylguanidine,
4-isobutyloxy-3-methylsulfonylbenzoylguanidine,
4-benzyloxy-3-methylsulfonylbenzoylguanidine,
4-(1-butylthio)-3-methylsulfonylbenzoylguanidine,
4-(1-butylsulfinyl)-3-methylsulfonylbenzoylguanidine,
4-(1-butylsulfonyl)-sulfamoylbenzoylguanidine,
4-(1-butylsulfonyl)-3-methylsulfonylbenzoylguanidine,
4-(2-chlorophenylthio)-3-methylsulfonylbenzoylguanidine,
4-phenoxy-3-methylsulfonylbenzoylguanidine,
4-cyclohexylthio-3-methylsulfonylbenzoylguanidine,
4-cyclohexylsulfinyl-3-methylsulfonylbenzoylguanidine,
4-cyclohexylsulfonyl-3-methylsulfonylbenzoylguanidine,
4-(1-piperidino)-3-sulfamoylbenzoylguanidine,
4-methoxy-3-sulfamoylbenzoylguanidine,
4-isobutyloxy-3-sulfamoylbenzoylguanidine,
4-benzyloxy-3-sulfamoylbenzoylguanidine,
4-(1-butylthio)-3-sulfamoylbenzoylguanidine,
4-(1-butylsulfinyl)-3-sulfamoylbenzoylguanidine,
4-(2-chlorophenylthio)-3-sulfamoylbenzoylguanidine,
4-cyclohexylthio)-3-sulfamoylbenzoylguanidine,
4-cyclohexylsulfonyl-3-sulfamoylbenzoylguanidine,
3-isopropylsulfamoyl-4-(1-piperidino)-benzoylguanidine,
3-(1-butylsulfamoyl)-4-(1-piperidino)-benzoylguanidine,
3-(N,N-di-1-butylsulfamoyl)-4-(1-piperidino)-benzoylguanidine,
3-(3-methoxypropylsulfamoyl)-4-(1-piperidino)-benzoylguanidine,
3-(3,5-dimethylpiperidino-N-sulfonyl)-4-(1-piperidino)-benzoylguanidine,
3-cyclopentylsulfamoyl-4-(1-piperidino)-benzoylguanidine,
4-(3-methoxy-1-propylamino)-3-methylsulfonylbenzoylguanidine,
4-(3-methoxy-1-propylamino)-3-sulfamoylbenzoylguanidine,
4-(N,N-di-1-butylamino)-3-methylsulfonylbenzoylguanidine,
4-(N,N-di-1-butylamino)-3-sulfamoylbenzoylguanidine,
4-N-pentamethyleneamino-3-methylsulfonylbenzoylguanidine,
4-N-pentamethyleneamino-3-sulfamoylbenzoylguanidine,
4-cyclopentylamino-3-methylsulfonylbenzoylguanidine,
4-cyclopentylamino-3-sulfamoylbenzoylguanidine,
4-(2-chlorophenylamino)-3-methylsulfonylbenzoylguanidine,
4-(2-chlorophenylamino)-3-sulfamoylbenzoylguanidine,
4-(4-methoxyphenylamino)-3-methylsulfonylbenzoylguanidine,
4-(4-methoxyphenylamino)-3-sulfamoylbenzoylguanidine,
4-(N-methyl-N-phenylamino)-3-methylsulfonylbenzoylguanidine,
4-(N-methyl-N-phenylamino)-3-sulfamoylbenzoylguanidine,
4-(2,4-dimethylamino)-3-methylsulfonylbenzoylguanidine,
4-(2,4-dimethylamino)-3-sulfamoylbenzoylguanidine,
4-(3-methylphenylamino)-3-methylsulfonylbenzoylguanidine,
4-(3-methylphenylamino)-3-sulfamoylbenzoylguanidine,
4-(4-methylphenylthio)-3-sulfamoylbenzoylguanidine,
4-(4-chlorophenylthio)-3-sulfamoylbenzoylguanidine,
4-(4-methoxyphenylthio)-3-sulfamoylbenzoylguanidine,
4-methyl-3-methylsulfonylbenzoylguanidine,
4-methyl-3-sulfamoylbenzoylguanidine.

EXPERIMENTAL SECTION

Example 1

4-Chloro-3-sulfamoylbenzoylguanidine hydrochloride 8.5 g of guanidine hydrochloride and then 5 g of methyl 4-chloro-3-sulfamoylbenzoate are added to a methanolic sodium methoxide solution, prepared from 1.9 g of sodium in 90 ml of methanol. After heating this mixture to 50°-60° C. under inert gas (nitrogen or argon) over the course of 30 hours, the solvent is removed by distillation, the solution is adjusted to pH 6 after taking up the residue with 2N acetic acid and is extracted with ethyl acetate. After acidifying the dried extract (drying over magnesium sulfate) using ethereal hydrochloric acid, the title compound is filtered off.

Colorless crystals, m.p. 305°-308° C.

Example 2

3-N,N-Diethylsulfamoyl-4-chlorobenzoylguanidine hydrochloride is obtained by reaction of 0.112 mol of guanidine, prepared from 10.7 g of guanidine hydrochloride and the equimolar amount of sodium methoxide in 70 ml of methanol, analogously to the procedure give in Example 1.

Colorless crystals, m.p. 202°-205° C.

Example 3

4-Chloro-3-methylsulfonylbenzoylguanidine hydrochloride is obtained analogously to the procedure given in Example 1 by reaction of 42.2 mmol of guanidine, prepared from 4.03 g of guanidine hydrochloride and 7.7 g of sodium bis(trimethylsilylamide) by heating to 50° C. in methanol over the course of 6 hours and analogous working-up.

Colorless crystals, m.p. 220° C. (dec.).

Example 4

3-Methylsulfonyl-4-(1-piperidyl)benzoylguanidine a) Disodium 5-carboxy-2-chlorobenzenesulfinate is obtained from 186 g of 5-carboxy-2-chlorobenzenesulfinic acid, prepared by reduction of 261 g of 5-carboxy-2-chlorobenzenesulfonyl chloride with 157 g of sodium sulfite in 700 ml of water at 70° C. at pH 9-10 and subsequent acidification using HCl, by neutralization with 67.6 g of caustic soda in 2 liters of water, removal of the latter by distillation and crystallization of the residue with acetone.

White crystal powder, m.p. >340° C.

b) Methyl 4-chloro-3-methylsulfonylbenzoate 52.9 g of the disodium salt prepared under 4a) are stirred at 50°-60° C. with 99.3 g of methyl iodide in 400 ml of anhydrous dimethylformamide over the course of 5 hours, the solvent is removed by distillation and, after stirring and washing the residue several times with water, the substance is filtered off.

White crystal powder, m.p. 150°-153° C.

c) 4-Chloro-3-methylsulfonylbenzoic acid 14.3 g of the methyl benzoate derivative prepared under 4b) are stirred at room temperature in 120 ml of methanol and 50 ml of 2N sodium hydroxide solution over the course of 6 hours, the solvent is removed by distillation, after dissolving the residue in water the solution is adjusted to pH 0-1 using 2N hydrochloric acid, and the substance is filtered off.

White crystal powder, m.p. 220°-224° C.

d) 3-Methylsulfonyl-4-(1-piperidino)benzoic acid 92 g of 4-chloro-3-methylsulfonylbenzoic acid are boiled under a reflux condenser in 460 ml of piperidine for 11 hours, the diluted with 800 ml of water and adjusted to pH 2 with conc. hydrochloric acid. After crystallization in an ice bath, the solid is filtered off.

Colorless crystals from ethanol, m.p. 234°-238° C.

e) 3-Methylsulfonyl-4-(1-piperidino)benzoyl chloride is obtained by refluxing 50 g of 3-methylsulfonyl-4-(1-piperidino)benzoic acid in 400 ml of thionyl chloride for 4 hours, careful removal of the solvent by distillation under reduced pressure and crystallization of the residue with dimethyl ether.

f) 3-Methylsulfonyl-4-(1-piperidino)benzoylguanidine 21.8 g of 3-methylsulfonyl-4-(1-piperidino)benzoyl chloride are stirred at 5°-10° C. with 31.4 g of guanidine in 200 ml of 1,2-dimethoxyethane under inert gas for 2 hours, about 200 ml of water are added with cooling and the mixture is adjusted to pH 6-7 using 2N HCl. After removing half the volume of the solution by distillation, the crystals are filtered off and recrystallized from methanol.

Colorless crystals, m.p. 210°-213° C. (dec.).

Example 5

3-Methylsulfonyl-4-(1-piperidino)benzoylguanidine dihydrochloride is obtained from 3-methylsulfonyl-4-(1-piperidino)-benzoylguanidine in 10 times its amount by weight of methanol by adding excess ethereal HCl and stirring the salt precipitate with cooling in an ice bath.

White crystal powder, m.p. 210°-214° C. (dec.).

Example 6

3-Methylsulfonyl-4-(1-piperidino)benzoylguanidine hydrochloride is obtained by treating 200 g of the dihydrochloride (Example 5) with the equivalent amount of a monovalent base (NaOH, NaHCO$_3$ N(C$_2$H$_5$)$_3$ etc.) in 1.3 to 1.4 liters of water or by simple recrystallization of the amount of substance given from 1.3-1.4 liters of water.

Colorless crystals, m.p. 235°-237° C.

Example 7

4-Chloro-3-N,N-dimethylsulfamoylbenzoylguanidine hydrochloride is obtained analogously to the procedure given in Example 1 by reaction of 2.77 g (0.01 mol) of methyl 4-chloro-3-dimethylsulfamoylbenzoate (m.p. 95°-96° C.) with 0.04 mol of guanidine in methanol and then analogous working-up.

White crystal powder, m.p. 224°-226° C. (dec.).

Example 8

4-Chloro-3-(1-piperidylsulfonyl)benzoylguanidine hydrochloride is obtained analogously to the procedure given in Example 1 from methyl 4-chloro-3-(1-piperidylsulfonyl)benzoate (m.p. 110°-112° C.) and guanidine in methanol as solvent.

White crystal power, m.p. 232°-234° C.

Example 9

3-N-Benzylsulfamoyl-4-chlorobenzoylguanidine hydrochloride is obtained analogously to the procedure given in Example 1 from methyl 3-N-benzylsulfamoyl-4-chlorobenzoate (m.p. 93°-95° C.) and guanidine in methanol as reaction medium.

White crystal powder, m.p. 224°-225° C.

Example 10

4-Sulfamoylbenzoylguanidine is obtained analogously to the procedure given in Example 1 from pentafluorophenyl 4-sulfamoylbenzoate, prepared from 4-sulfamoylbenzoyl chloride and pentafluorophenol in the presence of 1 mol of pyridine, with guanidine in methanol as reaction medium.

White crystal powder, m.p. 200° C. (dec.).

Example 11

4-Sulfamoylbenzoylguanidine hydrochloride is obtained by treating the compound prepared in Example 10 with ethereal HCl in ethyl acetate.

Colorless crystal powder, m.p. 282° C.

Example 12

4-N,N-Diethylsulfamoylbenzoylguanidine hydrochloride is obtained analogously to the procedure given in Example 1 from pentafluorophenyl 4-N,N-diethylsulfamoylbenzoate, prepared from 4-N,N-diethylsulfamoylbenzoic acid, pentafluorophenol, thionyl chloride and pyridine (m.p. 113°–114° C.), and guanidine in methanol as solvent and analogous working-up.

White crystal powder, m.p. 216°–218° C.

Example 13

4-(1-Piperidylsulfonyl)benzoylguanidine hydrochloride is obtained analogously to the procedure given in Example 1 from methyl 4-(1-piperidylsulfonyl)benzoate and guanidine in methanol as reaction medium.

White crystals, m.p. 281° C.

Example 14

4-Methylthiobenzoylguanidine hydrochloride is obtained analogously to the procedure given in Example 1 from methyl 4-methylthiobenzoate and guanidine in methanol as solvent.

White crystal powder, m.p. 255°–259° C.

Example 15

4-Phenylthio-3-sulfamoylbenzoylguanidine hydrochloride a) is obtained analogously to the procedure given in Example 1 from methyl 4-phenylthio-3-sulfamoylbenzoate and guanidine in methanol as solvent.

White crystal powder, m.p. 275°–283° C.

b) The methyl 4-phenylthio-3-sulfamoylbenzoate used is obtained by reaction of 4.4 g of methyl 4-fluoro-3-sulfamoylbenzoate (m.p. 127°–129° C.), prepared from 4-fluoro-3-sulfamoylbenzoic acid and thionyl chloride and subsequent methanol treatment, with 2.2 g thiophenol and 1.38 g of anhydrous and ground $K_2CO_2$ in 20 ml of anhydrous dimethylformamide for 2 hours at 80° C. and subsequent precipitation by addition of about 100 ml of water.

White crystals from methanol, m.p. 154°–157° C.

Example 16

3-Methylsulfonyl-4-phenylthiobenzoylguanidine hydrochloride a) is obtained analogously to the procedure given in Example 1 from methyl 3-methylsulfonyl-4-phenylthiobenzoate and guanidine in methanol as reaction medium and analogous working-up.

Colorless crystals, m.p. 279°–281° C.

b) The methyl 3-methylsulfonyl-4-phenylthiobenzoate used is prepared from methyl 4-chloro-3-methylsulfonylbenzoate by the procedure given in Example 15b).

White crystals, m.p. 155°–156° C.

Example 17

4-Phenoxy-3-sulfamoylbenzoylguanidine a) is obtained analogously to the procedure given in Example 1 (without HCl treatment) from methyl 4-phenoxy-3-sulfamoylbenzoate and guanidine in methanol.

White crystal powder, m.p. 178°–181° C.

b) The methyl 4-phenoxy-3-sulfamoylbenzoate used is obtained analogously to the procedure given in 15b) by reaction of 4-fluoro-3-sulfamoylbenzoic acid with phenol in DMF and in the presence of $K_2CO_2$ with stirring for 6 hours at 80° C.

White crystalline solid, m.p. 148°–151° C.

Example 18

3-Methylsulfonyl-4-N-morpholinobenzoylguanidine is obtained analogously to the procedure indicated in Example 4f) by reaction of 3-methylsulfonyl-4-N-morpholinobenzoyl chloride with guanidine in anhydrous tetrahydrofuran.

White crystal powder, m.p. 260° C. (dec.).

The 3-methylsulfonyl-4-N-morpholinobenzoyl chloride is obtained via several steps a) starting from 4-chloro-3-methylsulfonylbenzoic acid which is stirred at 110° C. in twice the amount by weight of morpholine for 5 hours and after taking up the reaction mixture in water, from which 3-methylsulfonyl-4-N-morpholinobenzoic acid (m.p. 252°–255° C. from methanol) is obtained after acidification using HCl.

b) 5 g of the 4-chloro-3-methylsulfonylbenzoic acid mentioned under a) are boiled under a reflux condenser in 50 ml of thionyl chloride for 2 hours and, after removing the liquid constituents by distillation, the desired benzoyl chloride derivative is crystallized in a diisopropyl ether/petroleum ether mixture.

m.p. 98°–102° C.

Example 19

3-Methylsulfonyl-4-N-pyrrolidinobenzoylguanidine is obtained analogously to the procedure given in Example 4f) by reaction of 5 g of 3-methylsulfonyl-4-N-pyrrolidinobenzoyl chloride with 3.4 g of guanidine in anhydrous tetrahydrofuran at room temperature, pouring into 200 ml of water and extraction with ethyl acetate. After removing the extracting agent by distillation, the solid is crystallized with methanol, dissolved in ethyl acetate and purified by column chromatography on silica gel (eluent ethyl acetate). After evaporating the eluent, the residue is crystallized with diisopropyl ether.

Colorless crystalline compound, m.p. 128°–135° C. (dec.).

The 3-methylsulfonyl-4-N-pyrrolidinobenzoyl chloride used is obtained via several steps starting from a) 4-chloro-3-methylsulfonylbenzoic acid analogously to the procedure given in Example 18a) by heating to 100° C. in pyrrolidine for 5 hours and analogous isolation of the resulting 3-methylsulfonyl-4-pyrrolidinylbenzoic acid; colorless crystals from ethanol, m.p. 228°–230° C.

b) The benzoic acid prepared in a) is converted into the desired 3-methylsulfonyl-4-N-pyrrolidinobenzoyl chloride (m.p. 137°–139° C.) analogously to Example 18b).

Example 20

4-N-Morpholino-3-sulfamoylbenzoylguanidine is obtained analogously to the procedure given in Example 1 from methyl 4-N-morpholino-3-sulfamoylbenzoate and guanidine by boiling in methanol for 4 hours, isolation of the title compound after extraction with ethyl acetate and purification by column chromatography on silica gel using ethyl acetate as eluent (without subsequent conversion into the hydrochloride with HCl).

White crystal powder, m.p. 239°–241° C.

The methyl 4-N-morpholino-3-sulfamoylbenzoate used as starting material is obtained by heating 2 g of methyl 4-fluoro-3-sulfamoylbenzoate with 1.5 g of morpholine in 8 ml of dimethylacetamide at 100° C. for 5 hours, subsequent precipitation of the substance by addition of water and crystallization of the amorphous ester precipitate with water.

m.p. 61°–64° C.

Example 21

3-Methylsulfonyl-4-(1-methyl-4-piperazino)benzoylguanidine is obtained analogously to the procedure given in Example 1 by reaction of 1 g of methyl 3-methylsulfonyl-4-(1-methyl-4-piperazino)benzoate and 1 g of guanidine in 25 ml of methanol as reaction medium at 60° C. for 6 hours. The compound precipitates out on allowing to stand overnight and is filtered off.

Pale yellow crystalline solid, m.p. 248°–250° C.

The methyl 3-methylsulfonyl-4-(1-methyl-4-piperazino)benzoate used as starting material is obtained via several reaction steps starting from a) 4.7 g of 4-chloro-3-methylsulfonylbenzoic acid and its reaction with 5.2 g of N-methylpiperazine in 15 ml of dimethylacetamide at 120° C. for 5 hours, distilling off the solvent, taking up the residue in water, acidifying with 2N hydrochloric acid and filtering off the precipitate. Crystalline solid, m.p. >300° C.

b) Reflux of the benzoic acid derivative prepared in a) in thionyl chloride, distillation thereof and reaction of the residue with methanol and triethylamine. After distilling off the solvent again and treating the residue with water, the desired methyl ester precipitates and is crystallized with diisopropyl ether.

White crystalline solid, m.p. 138°–145° C.

Example 22

4-N-Benzyl-N-methylamino-3-methylsulfonylbenzoylguanidine hydrochloride is obtained analogously to the procedure given in Example 4f) by reaction of 4.3 g of 4-N-benzyl-N-methylamino-3-methylsulfonylbenzoyl chloride with 5.2 g of guanidine in 30 ml of abs. tetrahydrofuran at 5° to 10° C. Before conversion with methanolic hydrogen chloride, the free benzoylguanidine of the title compound is purified by column chromatography on silica gel using a mixture of ethyl acetate (10 vol)+cyclohexane (5 vol)+chloroform (5 vol)+methanol (5 vol)+aq. NH₃ (1 vol) as eluent.

Colorless crystal powder, m.p. 234°–240° C.

The 4-N-benzyl-N-methylamino-3-methylsulfonylbenzoyl chloride described (oily amorphous product which is used without further purification steps) is obtained via several steps starting from 4-chloro-3-methylsulfonylbenzoic acid, which reacts in analogy to Example 21 a) with N-benzyl-N-methylamine to give 4-N-benzyl-N-methylamino-3-methylsulfonylbenzoic acid (m.p. 196°–202° C.,), and subsequent reaction with thionyl chloride.

Example 23

4-Benzylamino-3-methylsulfonylbenzoylguanidine acetate is obtained analogously to the method described in Example 4f) by reaction of 4-benzyl-3-methylsulfonylbenzoyl chloride with guanidine in anhydrous tetrahydrofuran. Working-up is carried out by acidifying with acetic acid to pH 4; after partially distilling off the solvent, in particular the THF component, 4-benzylamino-3-methylsulfonylbenzoylguanidine acetate precipitates in crystalline form.

Pale yellow crystalline solid having 2 melting points: m.p.₁ 163°–168° C., m.p.₂ 230°–232° C.

The 4-benzylamino-3-methylsulfonylbenzoic acid (m.p. 230°–235° C.) used as precursor is obtained in analogy to the reaction procedure described in Example 21 from 4-chloro-3-methylsulfonylbenzoic acid and benzylamine and the desired 4-benzyl-3-methylsulfonylbenzoyl chloride (m.p. 100°–104° C.) in the above analogy with thionyl chloride.

The following compounds of the formula I or their salts are obtained from the corresponding benzoyl chlorides of the formula II and guanidine in anhydrous tetrahydrofuran analogously to the procedure given in Example 4f):

Example 24

3-(3-Methyl-1-butylsulfonyl-4-N-piperidino-benzoylguanidine hydrochloride (m.p. 155° C./dec.) with disodium 2-chloro-5-carboxybenzenesulfinate as starting material via 3-methyl-1-butyl 4-chloro-3-(3-methyl-1-butylsulfonyl)benzoate (amorphous compound), 4-chloro-3-(3-methyl-1-butylsulfonyl)-4-N-piperidinobenzoic acid (m.p. 161°–165° C.) and 3-(3-methyl-1-butylsulfonyl)-4-N-piperidinobenzoyl chloride (oil).

Example 25

3-(1-Butylsulfonyl)-4-N-piperidinobenzoylguanidine dihydrochloride (m.p. 184° C./dec.) with disodium 2-chloro-5-carboxybenzenesulfinate as starting material via 1-butyl 3-(1-butylsulfonyl)-4-chlorobenzoate (oil), 3-(1-butylsulfonyl)-4-chlorobenzoic acid (m.p. 142°–146° C.), 3-(1-butylsulfonyl)-4-N-piperidinobenzoic acid (m.p. 156° C.) and 3-(1-butylsulfonyl)-4-N-piperidinobenzoyl chloride (oil).

Example 26

4-N-(1-Hexylamino)-3-methylsulfonylbenzoylguanidine

1.78 g of carbonyldiimidazole are added to a solution of 2.99 g of 4-N-(1-hexylamino)-3-methylsulfonylbenzoic acid in 40 ml of anhydrous tetrahydrofuran, the mixture is stirred at room temperature for 2 hours and at 45° C. for 1 hour and 4.13 g of guanidine are then added to the mixture at 20° C. The mixture is stirred at room temperature for 12 hours, the solvent is distilled off, the residue is adjusted to pH 6-7 using 2N HCl, the mixture is stirred in an ice bath for one hour, the solid is filtered off and, after washing with water, dissolved and allowed to recrystallize from ethanol.

Colorless solid, m.p. 135°-145° C.

Precursors of Example 26 starting from 4-chloro-3-methylsulfonylbenzoic acid via 4-N-(1-hexylamino)-3-methylsulfonylbenzoic acid (colorless crystals, m.p. 169° C.).

Example 27

3-N-Ethyl-N-isopropylsulfamoyl-4-(1-piperidino)benzoylguanidine is obtained analogously to the procedure indicated in Example 26 by reaction of 3-N-ethyl-N-isopropylsulfamoyl-4-(1-piperidino)benzoic acid, carbonyldiimidazole and guanidine.

Colorless crystals, m.p. 212° C.

Precursors of Example 27 starting from 3-chlorosulfonyl-4-fluorobenzoic acid via 3-N-ethyl-N-isopropylsulfamoyl-4-fluorobenzoic acid (m.p. 108°-115° C.) and 3-N-ethyl-N-isopropylsulfamoylbenzoic acid (m.p. 138°-140° C.).

Example 28

4-Amino-3-methylsulfonylbenzoylguanidine hydrochloride is obtained analogously to the procedure given in Example 1 by reaction of methyl 4-amino-3-methylsulfonylbenzoate and guanidine in methanol.

White crystal powder, m.p. 245°-248° C.

Precursors of Example 28 starting from 4-chloro-3-methylsulfonylbenzoic acid via 4-N-hydrazino-3-methylsulfonylbenzoic acid (m.p. 243°-245° C.) and its hydrogenolytic N—N cleavage with Raney nickel catalyst in methanol/aq. NH3 under normal pressure at room temperature to give 4-amino-3-methylsulfonylbenzoic acid (m.p. 258°-262° C.) and subsequent reaction with thionyl chloride and methanol to give methyl 4-amino-3-methylsulfonylbenzoate (m.p. 146° C.).

Example 29

1,1-Dimethyl-3-(3-methylsulfonyl-4-N-piperidinobenzoyl)guanidine 3.6 g of N-(3-methylsulfonyl-4-(1-piperidinobenzoyl)-carboxamidino-3,5-dimethylpyrazole-1-carboxylic acid are heated at 80° C. in 30 ml of 40% strength aqueous dimethylamine solution in an autoclave for 4 hours, and the crystalline precipitate is filtered off and recrystallized from ethanol.

Colorless crystals, m.p. 207° C.

Precursors of Example 29 starting from a solution of 2.92 g of 3-methylsulfonyl-4-N-piperidinobenzoyl chloride in 10 ml of ethyl acetate and its dropwise addition to a solution of 3,5-dimethylpyrazole-1-carboxamidine nitrate (97%, Aldrich) in 12.8 ml of 10% strength NaOH at 10°-15° C., stirring at room temperature for 2 hours, distilling off the solvent and recrystallizing the residue from ethyl acetate (colorless crystalline solid, m.p. 201°-202° C.).

Example 30

1-Methyl-3-(3-methylsulfonyl-4-N-piperidinobenzoyl)-guanidine is obtained analogously to the procedure given in Example 29 by reaction with 40% strength aqueous methylamine solution in an autoclave.

Colorless crystalline solid, m.p. 202°-203° C. (from ethanol).

Example 31

4-Chloro-3-(3-phenyl-1-propylsulfonyl)benzoylguanidine hydrochloride is obtained analogously to the procedure described in Example 26 by reaction of 4-chloro-3-(3-phenyl-1-propylsulfonyl)benzoic acid with guanidine and carbonyldiimidazole.

Colorless crystals, m.p. 178°-182° C. (dec.).

Precursors of Example 31 starting from 2-chloro-5-carboxybenzenesulfinic acid via 3-phenyl-1-propyl 4-chloro-3-(3-phenyl-1-propylsulfonyl)benzoate (viscous oil) and 4-chloro-3-(3-phenyl-1-propylsulfonyl)benzoic acid (colorless crystals, m.p. 126°-130° C.).

Example 32

4-(2,3-Dihydro-1-indolyl)-3-methylsulfonylbenzoylguanidine is obtained analogously to the procedure given in Example 26 from 4-(2,3-dihydro-1-indolyl)-3-methylsulfonylbenzoic acid, carbonyldiimidazole and guanidine (m.p. 136° C./dec.).

Precursors of Example 32 starting from 4-chloro-3-methylsulfonylbenzoic acid via 4-(2,3-dihydro-1-indolyl)-3-methylsulfonylbenzoic acid (m.p. 158° C.).

Example 33

3-(3-Phenyl-1-propylsulfonyl)-4-(1-piperidino)-benzoylguanidine dihydrochloride is obtained analogously to the procedure given in Example 26 by reaction of 3-(3-phenyl-1-propylsulfonyl)-4-(1-piperidino)benzoic acid, carbonyldiimidazole and guanidine.

Colorless solid, m.p. 160° C. (dec.).

Precursors: Starting from 4-chloro-3-(3-phenyl-1-propylsulfonyl)benzoic acid (see Example 31) via 3-(3-phenyl-1-propylsulfonyl)-4-(1-piperidino)benzoic acid (m.p. 170° C.).

Example 34

4-(N-2,4-Dichlorobenzyl-N-methylamino)-3-methylsulfonylbenzoylguanidine hydrochloride is obtained analogously to the procedure given in Example 1 by reaction of methyl 4-(N-2,4-dichlorobenzyl-N-methylamino)-3-methylsulfonylbenzoate and guanidine in methanol as solvent. (m.p.: 180° C.)

Example 35

4-(1-Piperidino)-3-sulfamoylbenzoylguanidine hydrochloride is obtained analogously to the procedure given in Example 26 from 4-(1-piperidino)-3-sulfamoylbenzoic acid, carbonyldiimidazole and guanidine.

Colorless crystalline solid, m.p. 236° C. (dec.).

Precursors starting from 4-fluoro-3-sulfamoylbenzoic acid via 4-(1-piperidino)-3-sulfamoylbenzoic acid (m.p. 246°-247° C.

The following compounds of the formula I shown are obtained analogously to the procedure given in Example 26 by reaction of a benzoic acid derivative of the formula II where X=OH, its activation with carbonyldiimidazole and subsequent reaction with guanidine:

Example 36

4-(3-Methoxy-1-propylamino)-3-methylsulfonylbenzoylguanidine hydrochloride

Colorless crystals, m.p. 167°-169° C.
(Precursors starting from 4-chloro-3-methylsulfonylbenzoic acid via 4-(3-methoxy-1-propylamino)-3-methylsulfonylbenzoic acid, m.p. 190° C./from ethanol.

Example 37

4-(3-Phenyl-1-propylamino)-3-methylsulfonylbenzoylguanidine

White crystal powder, m.p. 177°-178° C.
(Precursors starting from 4-chloro-3-methylsulfonylbenzoic acid via 4-(3-phenyl-1-propylamino)-3-methylsulfonylbenzoic acid (m.p. 172° C.).

Example 38

4-Isobutylamino-3-methylsulfonylbenzoylguanidine hydrochloride

White crystal powder, m.p. 163°-166° C.
(Precursors starting from 4-chloro-3-methylsulfonylbenzoic acid via 4-isopropylamino-3-methylsulfonylbenzoic acid, m.p. 180° C.).

Example 39

3-(3-Methoxy-1-propylsulfamoyl)4-(1-piperidino)benzoylguanidine hydrochloride

White crystal powder, m.p. 209°-211° C.
(Precursors starting from 4-chloro-3-chlorosulfonylbenzoic acid via 4-chloro-3-(3-methoxy-1-propylsulfamoyl)benzoic acid (m.p. 149°-150° C.) and 3-(3-methoxy-1-propylsulfamoyl)-4-(1-piperidino)benzoic acid (m.p. 138°-140° C.).

Example 40

3-Isopropylsulfamoyl-4-(1-piperidino)benzoylguanidine hydrochloride

White crystal powder, m.p. 209°-211° C.
Precursors starting from 4-chloro-3-isopropylsulfamoylbenzoic acid via 3-isopropylsulfamoyl-4-(1-piperidino)benzoic acid (m.p. 186°-188° C.).

Example 41

3-(1-Propylsulfamoyl)-4-(1-piperidino)benzoylguanidine hydrochloride

White crystal powder, m.p. 176° C. (dec.)
Precursors: starting from 4-chloro-3-(1-propylsulfamoyl)benzoic acid via 3-(1-propylsulfamoyl)-4-(1-piperidino)benzoic acid (m.p. 138°-139° C.).

Example 42

3-(3,5-Dimethyl-1-piperidinosulfonyl)-4-(1-piperidino)-benzoylguanidine

White crystal powder, m.p. 202°-204° C.
Precursors: starting from 3-chlorosulfonyl-4-fluorobenzoic acid via 3-(3,5-dimethyl-1-piperidinosulfonyl)-4-fluorobenzoic acid (m.p. 207° C.) and 3-(3,5-dimethyl-1-piperidinosulfonyl)-4-(1-piperidino)benzoic acid (m.p. 198° C.).

Example 43

3-Methylsulfonyl-4-(N,N-di-1-propylamino)benzoylguanidine hydrochloride

White crystal powder, m.p. 157°-9° C.
Precursors: starting from 3-methylsulfonyl-4-chlorobenzoic acid via 3-methylsulfonyl-4-(N,N-di-1-propylamino)benzoic acid (m.p. 122°-124° C.).

Example 44

4-Cyclopentylamino-3-methylsulfonylbenzoylguanidine

White crystal powder, m.p. 238°-40° C.
Precursors: starting from 4-chloro-3-methylsulfonylbenzoic acid via 4-cyclopentylamino-3-methylsulfonylbenzoic acid (m.p. 219°-222° C.).

Example 45

4-Ethylsulfonyl-3-N-pyrrolidinobenzoylguanidine hydrochloride

Analogously to Example 2 from methyl 4-ethylsulfonyl-3-N-pyrrolidinobenzoate and guanidine
m.p.: 180°-182° C.

Example 46

4-Phenylsulfonyl-3-N-pyrrolidinobenzoylguanidine hydrochloride

Analogously to Example 2 from methyl 4-phenylsulfonyl-3-N-pyrrolidinobenzoate and guanidine.
m.p.: 226°-228° C.

Example 47

Cyclohexylsulfonyl-3-N-pyrrolidinobenzoylguanidine

Analogously to Example 2 from methyl 6-cyclohexylsulfonyl-3-N-pyrrolidinobenzoate and guanidine. The initially obtained hydrochloride of the title compound is dissolved in H2O, and is precipitated as the free base by addition of 2N sodium hydroxide solution and filtered off with suction.
m.p.: 234°-36° C.

Example 48

4-Methylsulfonyl-3-N-pyrrolidinobenzoylguanidine

Analogously to Example 2 from methyl 4-methylsulfonyl-3-N-pyrrolidinobenzoate and guanidine.
m.p.: 165°-168° C.

Preparation of the precursors to Examples 45–48: Methyl 4-chloro-3-nitrobenzoate is used as starting material for the preparation of the corresponding methyl benzoates for Examples 45–48. Reaction with ethyl mercaptan (45), thiophenol (46), cyclohexyl sulfide (47) or methyl mercaptan (48) leads under standard conditions such as $K_2CO_3$ in DMF to the corresponding methyl 4-thio-3-nitrobenzoates which are oxidized to the corresponding 4-sulfonyl-3-nitrobenzoic acid esters with $H_2O_2$ in glacial acetic acid. After reduction of the 3-nitro group, the pyrrolidine radical is introduced with succinic anhydride and reduction with $NaBH_4$/BF$_3$.Et$_2$O:

10 g of methyl 3-amino-4-methylsulfonylbenzoate are stirred at 160° C. in the melt for 5 hours with 8.7 g of succinic anhydride. The solid residue is dissolved in methanol and stirred into water. The precipitated solid is filtered off with suction.

m.p.: 218°–220° C.

12.2 g of the methyl 4-methylsulfonyl-3-N-(2,5-dioxopyrrolidino)benzoate prepared in this way are dissolved in 100 ml of diglyme and cooled to 2° C. after addition of 14.5 ml of BF$_3$ etherate. 4.4 g of NaBH$_4$ are subsequently added and the mixture is stirred at this temperature for 5 hours. The mixture is then poured into ice/water and the precipitated methyl 4-methylsulfonyl-3-N-pyrrolidinobenzoate (m.p.: 96°–98° C.) is filtered off with suction. The corresponding benzoic acid esters for Examples 45, 46 and 47 are obtained analogously to this.

Example 49

4-Cyclohexylthio-3-methylsulfonylbenzoylguanidine

Analogously to Example 1, but using methyl 4-cyclohexylthio-3-methylsulfonylbenzoate as starting material.

m.p.: 201°–204° C.

Pharmacological data

K Strophanthidin-induced ventricular tachycardia in the dog

Method

Intravenous infusion of 3 μg/kg·min of ouabain leads to a lasting ventricular tachycardia (VT) within 40–60 minutes in pentobarbitone-anesthetized beagles. As soon as VT commences, the ouabain infusion is discontinued, but the VT endures for approximately 2 hours further and is monitored by continuous ECG checking. The substance to be tested is administered i.v. 10 min after completion of the ouabain infusion.

Results

In 4 of 5 dogs, 10 mg/kg of the compound from Example 34 led to a normalization of the ECG for 6–11 minutes.

We claim:

1. A benzoylguanidine of formula I

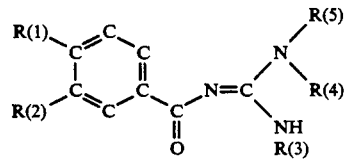

in which one of R(1) and R(2) is R(6)—S(O)$_n$— or

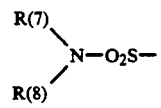

and the other of R(1) and R(2) is H, F, Cl, Br, I, C$_1$–C$_4$-alkyl, C$_1$–C$_4$-alkoxy, phenoxy which is unsubstituted or carries one to three substituents selected from fluorine, chlorine, methyl or methoxy, R(6)—S(O)$_n$ or

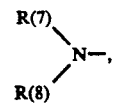

in which R(6) is C$_1$–C$_6$-alkyl, C$_5$–C$_7$-cycloalkyl, cyclopentylmethyl, cyclohexylmethyl or phenyl which is unsubstituted or carries one to three substituents selected from fluorine, chlorine, methyl or methoxy;

R(7) and R(8) are identical or different and are H or C$_1$–C$_6$-alkyl; or R(7) is phenyl-(CH$_2$)$_m$— where m=1–4, or phenyl which is unsubstituted or carries one or two substituents selected from fluorine, chlorine, methyl or methoxy; or R(7) and R(8) together are a straight or branched C$_4$–C$_7$ chain, R(3), R(4) and R(5) are hydrogen; and n is zero, 1 or 2;

and their pharmaceutically tolerable salts, with the proviso that said benzoylguanidine is not 3-methylsulfonyl-4-(1-piperidinyl)benzoylguanidine, 4-phenylthio-3-sulfamoylbenzoylguanidine, or 3-methylsulfonyl-4-phenylthiobenzoylguanidine.

2. A compound I as claimed in claim 1, in which:

R(1) is fluorine, chlorine, NR(7)R(8), R(6)—S(O)$_n$— or phenoxy,

R(2) is R(6)—S(O)$_n$— and R(7)R(8)N—SO$_2$— and in which n is zero, 1 or 2 and R(3), R(4) and R(5) are hydrogen, and in which R(6), R(7) and R(8) have the abovementioned meaning, and their pharmacologically tolerable salts.

3. A compound I as claimed in claim 1, in which:

R(1) is R(7)R(8)N— or R(6)—S(O)$_n$—, in which R(6) is alkyl having 1–3 carbon atoms or phenyl, n=zero and R(7) and R(8) are hydrogen or alkyl having 1–4 carbon atoms, or R(7) and R(8) together form a (C$_4$–C$_7$)-methylene chain and R(2) is CH$_3$—SO$_2$— or H$_2$N—SO$_2$—, R(3), R(4) and R(5) are hydrogen, and their pharmacologically tolerable salts.

4. A method of treating arrhythmias comprising administering to a host an effective amount for treating arrhythmias of compound I according to claim 1.

* * * * *

UNITED STATES PATENT AND TRADEMARK OFFICE
CERTIFICATE OF CORRECTION

PATENT NO. : 5,292,755
DATED : March 8, 1994
INVENTOR(S) : Englert et al.

It is certified that error appears in the above-indentified patent and that said Letters Patent is hereby corrected as shown below:

Column 1, line 17, after "or" insert the formula $R(7)R(8)N-SO2$;

Column 2, line 7, the formula $CH_3-CO_2-$ should read $CH_3-SO_2-$;

Column 4, line 25, that portion of the formula reading $R-On5$ should read $R-O_nS$.

Signed and Sealed this

Fifteenth Day of August, 1995

Attest:

BRUCE LEHMAN

Attesting Officer

Commissioner of Patents and Trademarks